United States Patent
Berger et al.

(10) Patent No.: US 9,626,613 B2
(45) Date of Patent: Apr. 18, 2017

(54) SYSTEM AND METHOD FOR COMPUTED RADIOGRAPHY USING NEAR FIELD COMMUNICATION TECHNOLOGY

(71) Applicant: Carestream Health, Inc., Rochester, NY (US)

(72) Inventors: Amir Berger, Kirvat Bialik (IL); Dmitry Teif, Nesher (IL); Yuval Ben-Ze'ev, Zichron Yaakov (IL)

(73) Assignee: Carestream Health, Inc., Rochester, NY (US)

(*) Notice: Subject to any disclaimer, the term of this patent is extended or adjusted under 35 U.S.C. 154(b) by 0 days.

(21) Appl. No.: 14/703,943

(22) Filed: May 5, 2015

(65) Prior Publication Data

US 2015/0324680 A1    Nov. 12, 2015

Related U.S. Application Data

(60) Provisional application No. 61/991,761, filed on May 12, 2014.

(51) Int. Cl.
*G06K 19/07* (2006.01)
*H04B 5/00* (2006.01)
*A61B 6/14* (2006.01)
*A61B 6/00* (2006.01)

(52) U.S. Cl.
CPC .......... *G06K 19/0723* (2013.01); *A61B 6/145* (2013.01); *A61B 6/4216* (2013.01); *A61B 6/4494* (2013.01); *H04B 5/0025* (2013.01)

(58) Field of Classification Search
USPC ............... 235/375; 340/10.1, 10.42, 40.52; 382/128
See application file for complete search history.

(56) References Cited

U.S. PATENT DOCUMENTS

| | | |
|---|---|---|
| 4,739,480 A | 4/1988 | Oono et al. |
| 4,960,994 A | 10/1990 | Muller et al. |
| 5,418,355 A | 5/1995 | Weil |
| 5,428,659 A | 6/1995 | Renner et al. |
| 5,757,021 A | 5/1998 | Dewaele |
| 6,359,628 B1 | 3/2002 | Buytaert |
| 6,381,416 B2 | 4/2002 | Manico et al. |

(Continued)

FOREIGN PATENT DOCUMENTS

| | | |
|---|---|---|
| EP | 0 727 696 | 8/1996 |
| EP | 2 492 831 | 8/2012 |

(Continued)

OTHER PUBLICATIONS

European Search Report, Application No. EP 15 16 7397, Oct. 6, 2015, 2 pages.

(Continued)

*Primary Examiner* — Allyson Trail

(57) ABSTRACT

A system and method for obtaining an intra-oral X-ray image of a patient. The system includes an information carrier plate having an affixed NFC/RFID tag. The NFC/RFID tag includes a memory. A primary tagging device reads and writes temporary information into the tag's memory over a first communication channel. A scanner is in communication with a secondary tagging device to read and write the temporary information saved in the tag's memory over a second communication channel.

5 Claims, 12 Drawing Sheets

(56) References Cited

U.S. PATENT DOCUMENTS

| | | |
|---|---|---|
| 7,095,034 B2 | 8/2006 | Haug et al. |
| 7,211,785 B1 | 5/2007 | Berger et al. |
| 7,319,396 B2 | 1/2008 | Homanfar et al. |
| 7,518,518 B2 | 4/2009 | Homanfar et al. |
| 2009/0248437 A1 | 10/2009 | Gucciardi et al. |
| 2010/0004950 A1 | 1/2010 | Bajko et al. |
| 2010/0148723 A1 | 6/2010 | Cook et al. |
| 2012/0001737 A1* | 1/2012 | Berger ............... A61B 6/145 340/10.42 |
| 2012/0088998 A1* | 4/2012 | Bardy ............... A61B 5/0006 600/382 |
| 2012/0173318 A1 | 7/2012 | Lee et al. |
| 2012/0183183 A1* | 7/2012 | Jouhikainen ........ A61B 1/00 382/128 |
| 2012/0326847 A1 | 12/2012 | Strauman |
| 2013/0193206 A1 | 8/2013 | Berger et al. |
| 2013/0201006 A1* | 8/2013 | Kummetz ............ H04K 3/68 340/10.1 |
| 2013/0329860 A1 | 12/2013 | Nonaka |
| 2014/0112439 A1 | 4/2014 | Berger et al. |
| 2014/0121489 A1 | 5/2014 | Kommu Chs |
| 2014/0191852 A1* | 7/2014 | Inglese ............... A61B 6/145 340/10.52 |

FOREIGN PATENT DOCUMENTS

| | | |
|---|---|---|
| JP | 2013/050823 | 3/2013 |
| WO | 2012/067640 | 5/2012 |
| WO | 2012/141437 | 10/2012 |

OTHER PUBLICATIONS

S. Clark, "Identive and WPG to share x-rays via NFC", NFC World, 2012, internet address http://www.nfcworld.com/2012/03/12/314303/identive-and-wpg-to-share-x-rays-via-nfc/.

\* cited by examiner

SYSTEM AND METHOD FOR COMPUTED RADIOGRAPHY USING NEAR FIELD COMMUNICATION TECHNOLOGY

CROSS REFERENCE TO RELATED APPLICATIONS

This application claims the benefit of U.S. Ser. No. 61/991,761, provisionally filed on May 12, 2014, entitled "SYSTEM AND METHOD FOR COMPUTED RADIOGRAPHY USING NEAR FIELD COMMUNICATION TECHNOLOGY", in the names of Berger et al, which is incorporated herein in its entirety.

TECHNICAL FIELD

The present invention relates to identification of medical items. More particularly, the present invention refers to identification, monitoring, and tracking of flexible information carrier plates used in computed radiography when the plates are circulating from exposure to X-rays to scanning. In particular, the present invention refers to identification, monitoring, and tracking of flexible information carrier plates that are used in intra-oral dental imaging.

BACKGROUND

The use of information carrier plates (also referred to as phosphor or phosphor storage plates) for obtaining visually perceptible contrast upon exposure to X-rays is known in the art as computed radiography (CR) and is described for example in U.S. Pat. No. 7,211,785 (Berger).

The imaging cycle employing such information carrier plates comprises juxtaposing the plate nearby a specific part of the body (e.g., leg, arm, tooth, and the like) and then exposing the plate to X-rays in order to obtain an image from stored radiation energy. Following exposure, the plate is then removed from the patient and the latent image that is stored thereon is scanned by a laser beam or other energy source to stimulate emission of the stored energy and to form corresponding image data from the emitted energy. After the plate has been scanned, the obtained image data can be displayed and stored for further examination. The exposed and scanned plate is then erased and can be reused in a subsequent imaging cycle.

U.S. Pat. No. 5,428,659 (Renner) describes a digital memory configured as a PCB (printed circuit board).

U.S. Pat. No. 7,319,396 (Homanfar) and U.S. Pat. No. 7,518,518, (Homanfar) describe using an RFID tag.

U.S. Pat. No. 7,095,034 (Haug) describes image carriers enclosed in cassettes, with an RFID tag affixed to the cassette.

U.S. Pat. No. 5,418,355 (Weil) describes storage media enclosed in a cassette wherein the media is provided with an identification bar code.

U.S. Pat. No. 4,739,480 (Oono) describes a label adhered to the image storage panel, with the panel stored in a cassette.

U.S. Pat. No. 6,359,628 (Buytaert), U.S. Pat. No. 5,757,021 (Dewaele) and EP 0727696 (Dewaele) describe media contained in a rigid cassette with an RFID tag attached to the cassette.

U.S. Pat. No. 4,960,994 (Muller) describes media that is used in association with a cassette and with a memory affixed to the cassette in a predetermined location.

U.S. Pat. No. 6,381,416 (Manico) describes use of an RFID tag in association with photographic film used in consumer photography, for example, for establishing conditions to be selected for processing of the film.

U.S. 2012/0001737 (Berger) describes a system and a method for computed radiography employing flexible information carrier plates having an affixed RFID tag with a memory.

U.S. 2012/326847 (Strauman) describes secure NFC tag management method and system for initiating a desired function in a mobile communication device.

WO 2012/067640 (Villa-Real) describes methods and systems employing NFC mobile component.

EP 2492831 (Chen) describes biomedical device with NFC unit, e.g. smart phone for user identification, biomedical data measurement, biomedical data upload/download, biomedical data management and remote medical care.

WO 2012/141437 (Kim) describes an apparatus for measuring and management biometrical medical information for verification identity while employing NFC unit, e.g. smart phone.

U.S. 2009/248437 (Gucciardi) describes systems and methods for implementing portable medical record.

U.S. 2010/004950 (Bajko) describes a system and method for usage of personal medical records in mobile devices.

JP 2013050823 (Higashi) describes a medical information medical system for exchange of information between a patient and a medical institution.

Sarah Clark is the author of the article "Identive and WPG share x-rays via NFC" published in the Internet on 12 March, 2012, which Internet address is http://www.nfc-world.com/2012/03/12/314303/identive-and-wpg-to-share-x-rays-via-nfc/

Despite attempts to employ RFID technology in various applications, including computed dental radiography, there is room for improvement.

SUMMARY OF THE INVENTION

The present invention is intended to provide a convenient and reliable solution for identifying, monitoring and tracking flexible information carrier plates used in intra-oral dental computed radiography in order to prevent their inadvertent or intentional mismatch.

One object of the present invention is to provide a new, convenient and economical solution for dental radiography employing an NFC read/write component and flexible information carrier plates provided with an RFID/NFC tag being accessible using wireless communication between the tag and the NFC read/write component, to enable identification, monitoring, and tracking of the information carrier plates, irrespective whether the plates are enclosed in disposable or in re-usable envelopes.

Still further object of the present invention is to provide a new, convenient and reliable solution for dental radiography employing an NFC read/write component and flexible information carrier plates provided with an RFID/NFC tag, in which communication between the NFC read/write component and the RFID/NFC tag is possible via existing mobile telephone net, or by virtue of Wi-Fi communication, or Bluetooth communication or any other suitable wire or wireless communication.

Another object of the present invention is providing a new method and system for dental computed radiography employing RFID/NFC tags that can be attached to flexible information carrier plates, irrespective of plate size or specific location or side of the plate.

A further object of the present invention is providing a new method and system for dental computed radiography employing RFID/NFC tags having memory and NFC reader/writer component, wherein the memory of the tag can be read and loaded by the NFC reader/writer component with both permanent and temporary identification information.

Still further object of the present invention is providing a new method and system for dental computed radiography employing RFID/NFC tags and NFC/reader/writer component, wherein the reader/writer component is a mobile communication device, e.g. smartphone or tablet.

Yet another object of the invention is providing a new method and system for computed dental radiography employing RFID/NFC tags in which memory of the NFC tags can be loaded with identification information concerning the information carrier plate itself, as well as with identification information concerning a dental treatment to be carried out.

Another object of the invention is providing a new method and system for computed dental radiography in which the identification information concerning dental treatment comprises at least data associated with a patient and with specific conditions for examination.

Still another object of the invention is providing a new method and system for dental computed radiography in which the identification information concerning the information carrier plate comprises e.g., plate size and type, manufacturing date, first scan date (activation date), scan count, job number, resolution, destination address and scan status.

Still another object of the invention is providing a flexible, information carrier plate for intra-oral computed radiography, the plate being substantially flat and defined by two opposite sides, the plate bearing an RFID/NFC tag affixed immediate to one of its opposite sides, the RFID/NFC tag comprising a memory for storing information therein.

According to one embodiment, the present invention provides a system for obtaining an intra-oral X-ray image of a patient. This system comprises one or more information carrier plates, each information carrier plate having a NFC/RFID tag affixed to the information carrier plate, said NFC/RFID tag having a memory. The system further comprises at least one primary tagging device that is operable to read and write temporary information into the memory of the NFC/RFID tag over a first wireless communication channel. And the system further comprises at least one scanner in communication with a secondary tagging device that is operable to read and write temporary information saved in the memory of the NFC/RFID tag over a second wireless communication channel, wherein the at least one primary tagging device is a mobile communication device.

For a better understanding of the present invention as well of its benefits and advantages, reference will now be made to the following description of various exemplary embodiments taken in combination with the accompanying drawings.

DETAILED DESCRIPTION OF THE INVENTION

Figure 1:
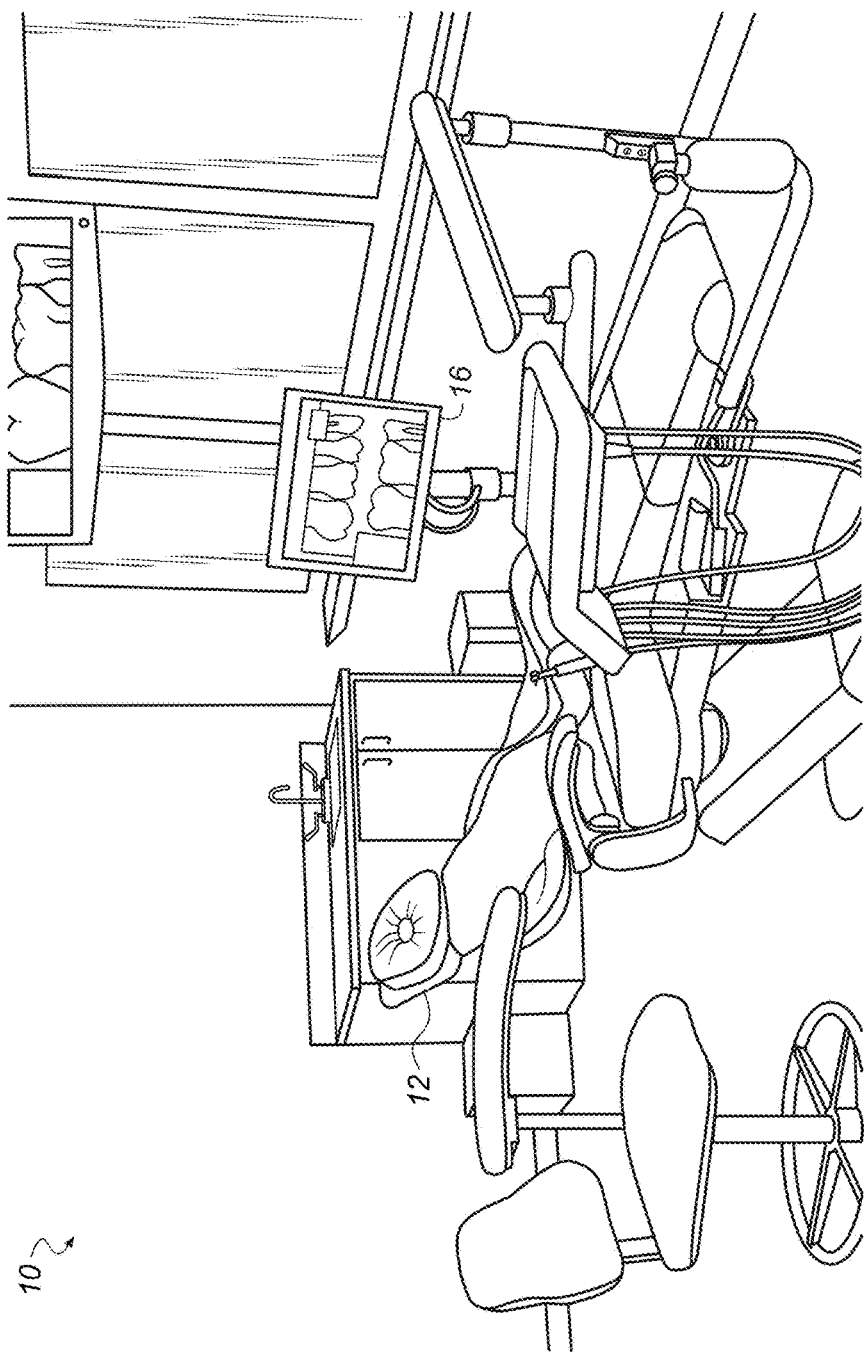
FIG. 1 shows a general treatment room used by a practitioner and provided with a chair working station.

The present invention relates to identification of medical items to prevent their intentional or inadvertent mismatch during use or reuse. More particularly, the present invention refers to identification, monitoring, and tracking of flexible information carrier plates used in computed radiography when the plates are circulating from exposure to X-rays to scanning. Even more particularly, the present invention refers to identification, monitoring, and tracking of flexible information carrier plates that are used in intra-oral dental imaging.

It can be appreciated that each plate must be properly tracked throughout the imaging cycle as the plate circulates from X-ray exposure, to scanning, to erasure, and to re-use. That is, it must be possible, at each stage in this process, to know specific plate identification information as well as patient identification information and identification information concerning specific treatment with which a plate is associated.

This is relevant for general medical computed radiography (CR) and becomes especially complex for intra-oral dental computed radiography applications. In dental clinics, large numbers of patients undergo X-ray examination, and therefore a large number of information carrier plates can be in circulation at any one time, thus increasing the probability for mismatch between a particular plate and the patient and treatment data associated with the plate, as well as with the obtained image on the plate. The probability for mismatch is especially high in a working environment where several treatment rooms, each equipped with an X-ray generator, share the same scanning device. Any mismatch can result in confusion, delay, waste, incorrect diagnosis, and the need to repeat an exposure in some cases. Other possible errors that can occur due to mismatch include inadvertent re-exposure of a plate that has not yet been erased.

The likelihood for error and the impact of an error can be further compounded when a full mouth scan is executed. This dramatically increases the number of plates used for a particular patient and requires careful tracking to avoid mistakes.

With intra-oral dental computed radiography, the mismatch between CR plates is not easily detectable to the eye, since different teeth can have a relatively similar appearance. The likelihood of confusion is high when compared with other medical radiography applications that image larger or more distinctive parts of the body about which there can be much less confusion.

Thus, positive and unequivocal identification, as well as monitoring and tracking of information carrier plates, is desired in computed radiography in general, and in intra-oral dental computed radiography in particular, since it helps to prevent patient mismatch and other errors.

In intra-oral dental computed radiography, the exposed information carrier plates are usually placed on a flat holder that is divided into cells referring to different teeth. A technician puts the CR carrier plates on the holder such that a certain plate occupies a certain cell. The pattern of the cells corresponds to the pattern of a template that is filled in by the dental practitioner before submitting the plates to X-ray exposure. The plates are moved from the treatment station to an X-ray station and then to a scanning station, lying on the holder in the order corresponding to the template pattern. In particular situations, this arrangement can be unreliable, for example, the plates can fall from the holder during handling. Their correct re-attribution to the corresponding cell can be complicated if the plates are not provided with some type of identification means.

Radio Frequency Identification Devices (RFID devices) are known for identification, tracking, and monitoring of various items. RFID tracking is used for identifying various items, like consumer goods, reusable and disposable items, people, animals and the like. This identification technology has been implemented in various technical and non-technical fields, including medicine.

An RFID system comprises two main components: (i) a transponder associated with an item to be identified, and (ii) an interrogator, separated from the transponder by a short distance, that comprises an antenna, a transceiver and a processing device. The interrogator component sends RF energy and an interrogating signal (if necessary) to the transponder and then receives an RF response signal from the transponder. The received signal is transferred to the processing device and is read.

The transponder, or so-called RFID tag, is affixed by a suitable method to the item to be identified and comprises an integrated circuit containing RF circuitry. This circuitry serves as memory for storing information to be transmitted as a signal to the processing device in the interrogator. The RFID tag also comprises an antenna for transmitting this signal. Reading the signal that has been sent by the transponder allows the item bearing the tag to be identified and monitored.

Some clinics have more than one room and are equipped with a single scanner shared by several practitioners.

It would be desirable that instead of having a dedicated computer with monitor at each processing and acquisition station, the possibility for tagging would be readily available at any location, where the carrier plates are available, and in particular at the location where the plates are exposed to X-ray. Furthermore, it would be desired that both the data being written in the memory of the tag during the tagging procedure as well as the image obtained by scanner could be readily displayable on the tagging device itself instead of or in addition to the displaying the image on the monitor available at the processing and the acquisition station.

There is known in the art so-called Near Field Communication technology, or briefly NFC technology. This technology is defined by a set of standards developed for mobile communication devices. The NFC technology concerns establishing of radio communication between mobile communication devices, such like smartphones, tablets, etc. The communication is established by touching the communication devices together or bringing them into close proximity, usually no more than a few centimeters. The NFC technology operates at 13.56 MHz and in fact it is an extension of High Frequency (HF) RFID standard. Seeing the NFC shares many physical properties with RFID such as one way communication and the ability to communicate without a direct line of sight the existing MD tags could be used for the purpose of the NFC technology.

Applicants recognize that there is room for improvement by providing an NFC solution tailored for specific workflow requirements of intra-oral dental computed radiography.

It is noted that the present invention is not limited to medical radiography in general or to intra-oral dental radiography in particular. The present invention is suitable for other medical and non-medical applications as well.

In the context of the present disclosure, the equivalent terms "flexible information carrier plate", "flexible plate", "CR plate" or simply "plate" refer to photo-stimulable phosphor plates (PSP plates) that are used for image storage in the computed radiography CR arts, deployed in a manner analogous to the photographic plates that they have replaced in many applications. The information carrier plate is considered flexible when it has at least some degree of conformance to curvatures useful for intra-oral imaging.

In the context of the present disclosure, the term "scanner" or "scanning device" refers to a device or apparatus that is capable of obtaining stored image data from the flexible information carrier plate following exposure of the plate. The scanner typically stimulates the phosphor storage media using a laser beam. As the beam energy passes over the plate surface, it frees electrons "trapped" in "color centers" in the crystal lattice of the X-rayed phosphor plate. The light emitted during laser stimulation can be collected and the resulting signal converted into a digital image by a computer or other dedicated logic processor. The location at which the scanner is deployed is referred to as a scanning station.

In the content of present disclosure the term "mobile communication device", or "mobile device", or "handheld computer", or "mobile communication component", or simply "handheld" refers to a small, handheld computing device, having a display screen preferably with touch input and/or a miniature keyboard and weighing less than 1 kg. Apple, Nokia, LG, BlackBerry, Samsung are just a few examples of the many manufacturers that produce these types of devices.

A handheld computing device has an operating system (OS), and can run various types of application software, known as apps. Most handheld devices can also be equipped with Wi-Fi, Bluetooth, and GPS capabilities that can allow connections to the Internet.

Early developed pocket-sized mobile devices were joined in the late 2000s by larger but otherwise similar tablet computers having a touch-screen interface and in the content of present disclosure the term "tablet" also has the meaning of "mobile communication device".

Referring now to FIG. 1, there is shown a typical dental treatment room 10 of a practitioner. The treatment room inter alia comprises a treatment chair 12 having a console with various instruments as required for dental treatment, e.g. intra-oral treatment.

The treatment room is preferably equipped with a suitable interface terminal that serves as a processing and acquisition station for input output, and management of data and possibly including a keyboard with mouse. It is not shown specifically but should be appreciated that the interface communicates over a network, for example, via a local Ethernet network, with a suitable server providing access to a database and a software application enabling management of medical and personal data related to a medical case. The application also allows acquisition, viewing, and processing of images obtained after scanning, archiving the images and related data, and other functions. In an alternate embodiment, such as in a small clinic, the interface may communicate with a local computer workstation or personal computer (PC), instead of with a networked server.

The treatment room is suitable for computed intra-oral dental radiography and it can be equipped with a monitor 16, e.g., a LCD (Liquid Crystal Display) for displaying images acquired after X-ray exposure and scanning. It is not shown in FIG. 1 but should be appreciated that a plurality of flexible information carrier plates are available, typically stored in the vicinity of the treatment chair.

While not shown in FIG. 1, it would be appreciated that the treatment room can also comprise an X-ray generator, which may be situated either in the treatment room itself or adjacent thereto. In a small treatment room, a scanner can also be provided for obtaining the stored image data obtained after exposing the information carrier plates to X-rays. However location of the scanner within the treatment room is not compulsory, since the practitioner can alternately share the same scanner that is situated apart from the treatment room.

In the present disclosure, the treatment room is alternately referred to as a working station. If the working station is equipped with a scanner dedicated solely to this station, then the possibility for mismatch of the plates is less likely. This possibility, however still exists and therefore it would be desirable to render the plates identifiable in some way even for such a basic system.

Figure 2:
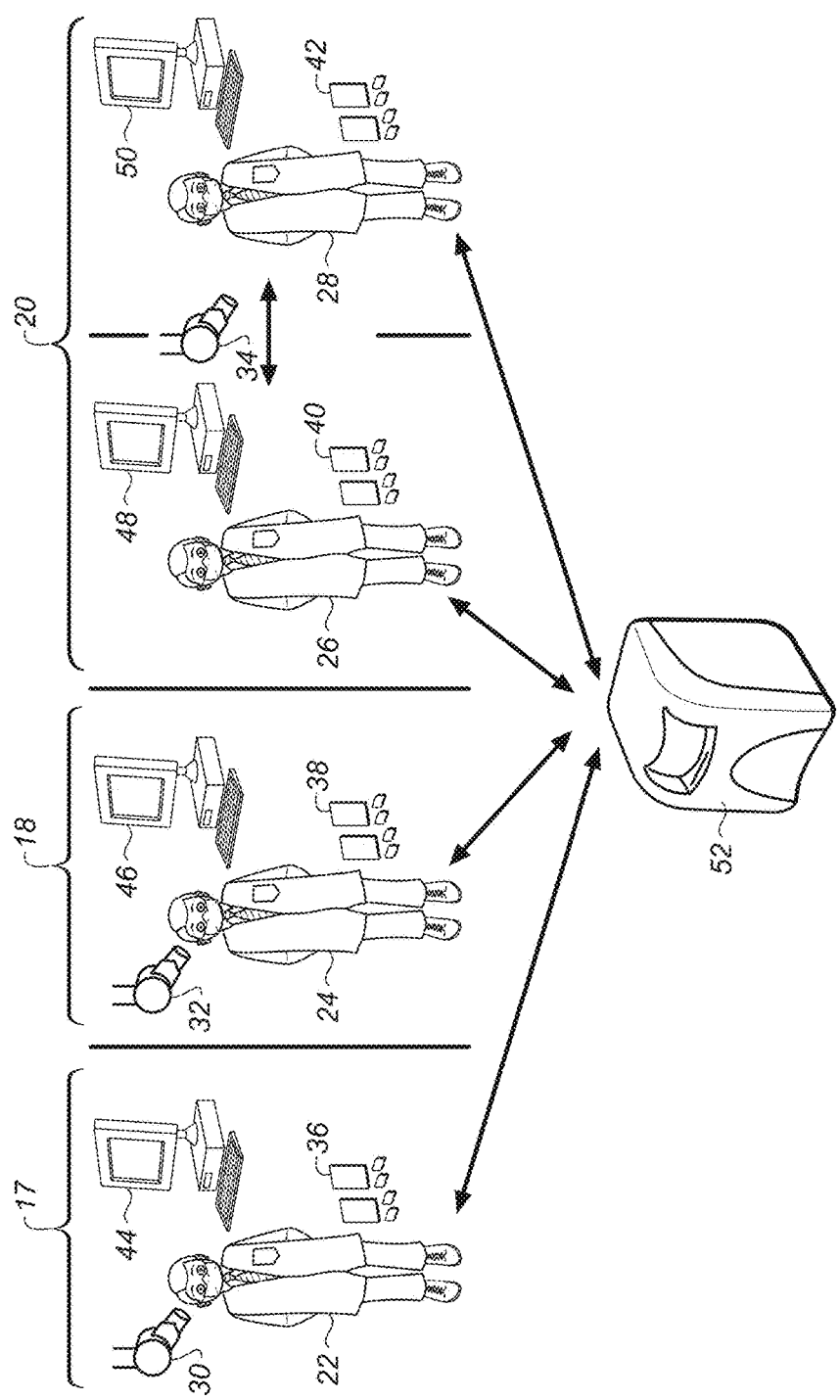
FIG. 2 depicts example of working environment in which in the same clinic several practitioners occupy separate working stations and share the same scanning station.

FIG. 2 shows a schematic of another exemplary working environment for infra-oral computed radiography. This environment is more prone to mismatch than the single working station of FIG. 1 and therefore requires more careful identification of the information carrier plates. This working environment comprises a plurality, for example three, separate working stations 17, 18, 20. Working stations 17 and 18 are used by two respective practitioners 22 and 24. Working station 20 is used by two neighboring practitioners 26 and 28. Each working station is equipped with a respective X-ray generator 30, 32, 34. The generator 34 is shared by practitioners 26 and 28.

Each practitioner has sufficient stock 36, 38, 40, 42 of flexible information carrier plates, here designated as media. Each working station has a computer with respective LCD monitor 44, 46, 48, 50 and respective keyboard and mouse.

It is also seen in FIG. 2 that working stations communicate with a common scanner 52 installed in a separate room, e.g., a disinfection room or a surgery room. This scanner is shared by all practitioners and therefore, in order to organize the workflow efficiently, the scanning step should be synchronized with the X-ray exposure step carried out in the working stations so that each practitioner reserves the scanner for plate processing before sending the exposed plates to scanning.

In an environment such as that shown in FIG. 2, a substantial number of exposed plates requiring scanning can be generated (especially where full mouth imaging is needed for one or more patients). The likelihood of mismatch is high. In the event of such a mismatch, the scanning step constitutes a bottleneck to the whole workflow. Therefore, in a working environment of this type wherein a single scanner is shared by several working stations, it is especially important to prevent mismatch between plates as they circulate between many working stations and scanner.

Figure 3:
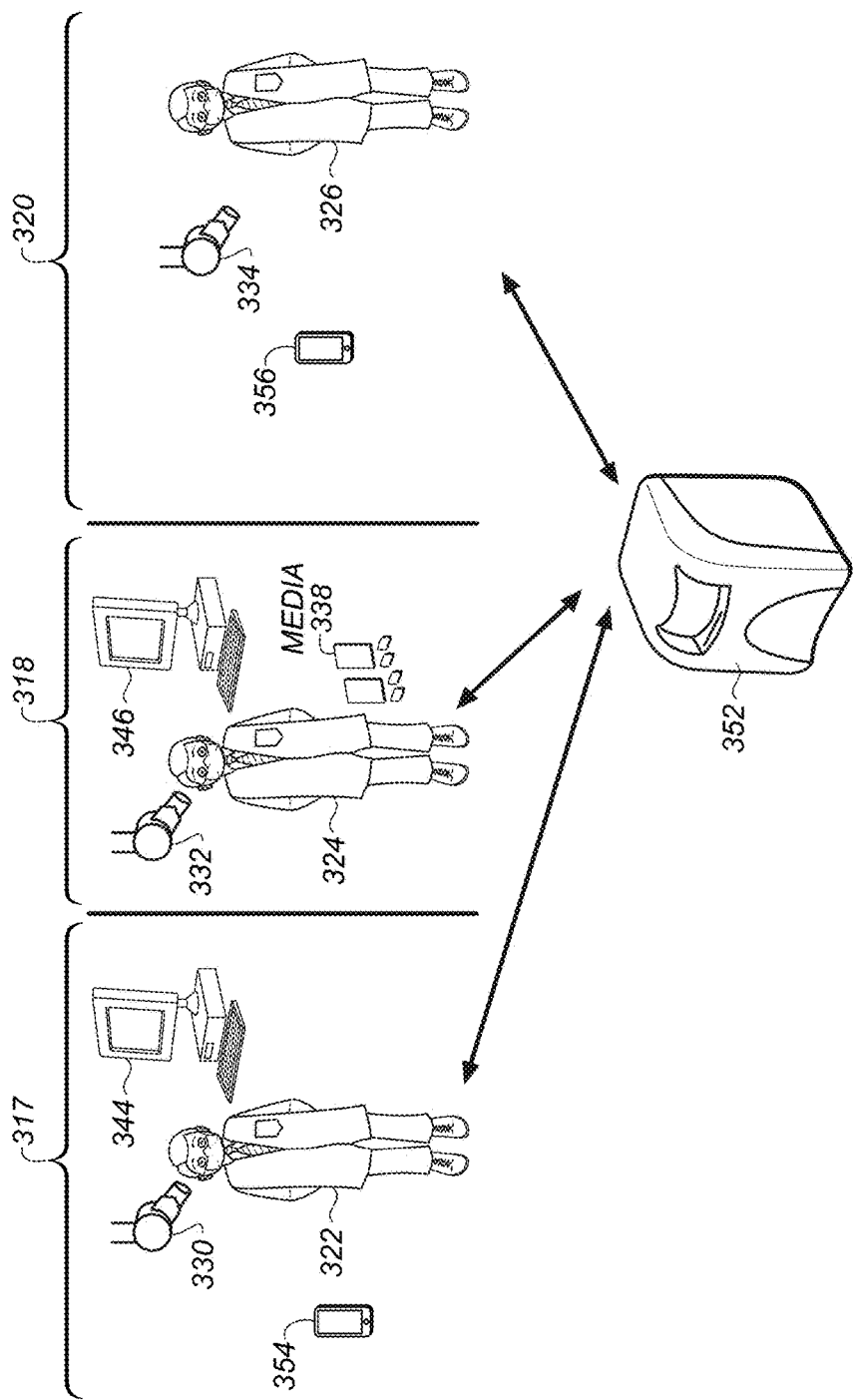
FIG. 3 shows another example of working environment in which in the same clinic several practitioners occupy separate working stations and share the same scanning station.

Still further example of the working environment is depicted in FIG. 3, where are seen three adjacent working stations 317, 318, 320, each of them being equipped with a respective X-ray generator 330, 332, 334 and practitioner 322, 324, 326. It is seen that two working stations, namely 317 and 318 are provided with a respective computer 344, 346, having keyboard and mouse as is necessary for processing and acquisition of data, while the working station 320 is not equipped with the computer. Shown schematically and designated at 338 a stock of flexible information carrier plates is available at working station 318.

It should be appreciated that the rest of the working stations is also provided with respective stock of the flexible carrier plates.

Each working station is in communication with a common scanner 352.

It is seen further that at working station 317 and 320 a mobile communication device, e.g. smartphone 354, 356 is available, which communicates at frequency 13.56 MHz with the server and with the scanner. By virtue of this provision processing and acquisition of data is possible in addition to or instead of the data exchange provided by computers.

In accordance with the system, the mismatch between the flexible carrier plates can be prevented by providing the plates with identification means rendering them immediately attributable by virtue of communication with the mobile communication device. It would then be possible to improve the workflow and to proceed through the treatment plan more efficiently without disrupting daily operation.

In accordance with the system, the information carrier plates are provided with an affixed RFID transponder or tag that has a memory loadable with both permanent and temporary information and which can be transmitted by wireless communication by virtue of the NFC technology. The RFID tag affixed to the plate enables memory on the information carrier plate to be in communication with the mobile communication device operating at frequency 13.56 MHz. When the mobile communication device communicates with the RFID tag attached to the carrier plate it is capable of reading data stored in the memory of the RFID tag as well as capable of loading the RFID tag's memory with permanent and/or temporary data and/or updating the temporary information stored in the memory. This capability would be further referred-to as "tagging" and one can appreciate that the mobile communication device in fact constitutes a mobile tagging device which by virtue of the NFC technology communicates with the RFID tag. Therefore a RFID tag capable inter alia to communicate at frequency 13.56 MHz or a dedicated RFID tag designed specifically to communicate at this frequency with the mobile communication device will be referred-to here as a RFID/NFC tag.

Furthermore, in accordance with the invention the other useful capabilities of the mobile communication device would be employed. So, for example one of such capabilities is display of images on the screen of the mobile communication device. By virtue of this provision it would be possible to use electronic templates during the tagging step as well as displaying the scanned images immediately on the tagging device without necessity to have a dedicated computer or display at the processing and acquisition station.

By virtue of the NFC technology the mobile communication device can be situated at any physical location in the practitioner's clinic so long as the mobile communication device can be brought in close proximity to the RFID/NFC tag affixed to a carrier plate. Thus the mobile communication device not necessarily should be situated at the processing and acquisition station or near the scanner. In particular, mobile communication device can be located at the same place, where the X-ray generator is situated, irrespective whether this location is equipped or not with computer and monitor.

In accordance with the system, the mobile communication device has a data management application software, which is either compatible with the existing data management software or is a dedicated software that makes possible communication between the mobile communication device and the server either via Wi-Fi channel, or via Bluetooth channel, or via a local net, or wire or via a cable channel. By virtue of this provision mobile communication device is automatically detected by the server and easily communicates with it. An example of suitable data management software is PCACQ software.

The tag's affixed memory can be loaded with the information and the stored information can be read using the mobile communication device.

Furthermore, in accordance with the system, the application software installed in the mobile communication device allows to be in wireless communication with the scanner such that digital images produced by the scanner could be displayed on the display of the mobile communication device.

Figure 5:
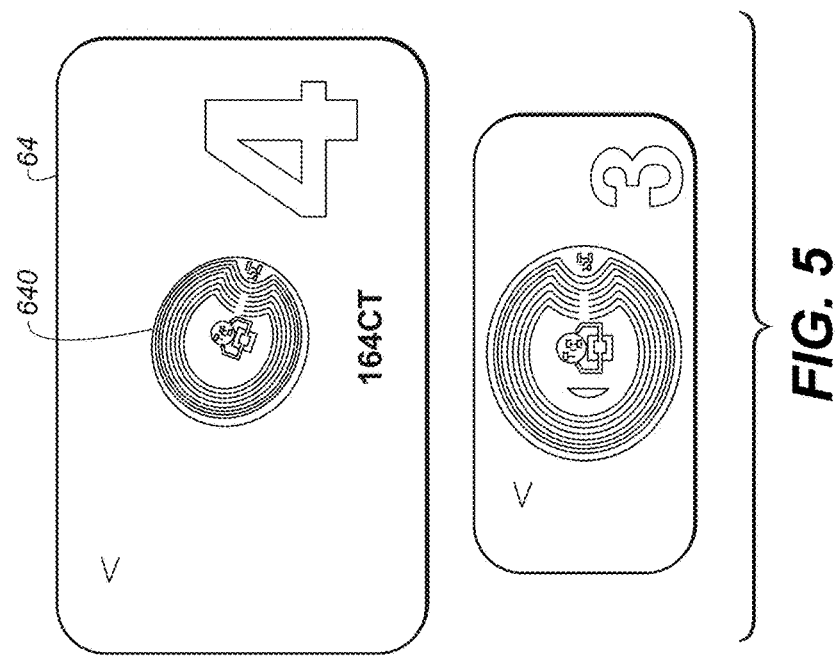
FIGS. 4, 5 show flexible carrier plates provided with RFID/NFC tags in accordance with the present invention.
Figure 4:
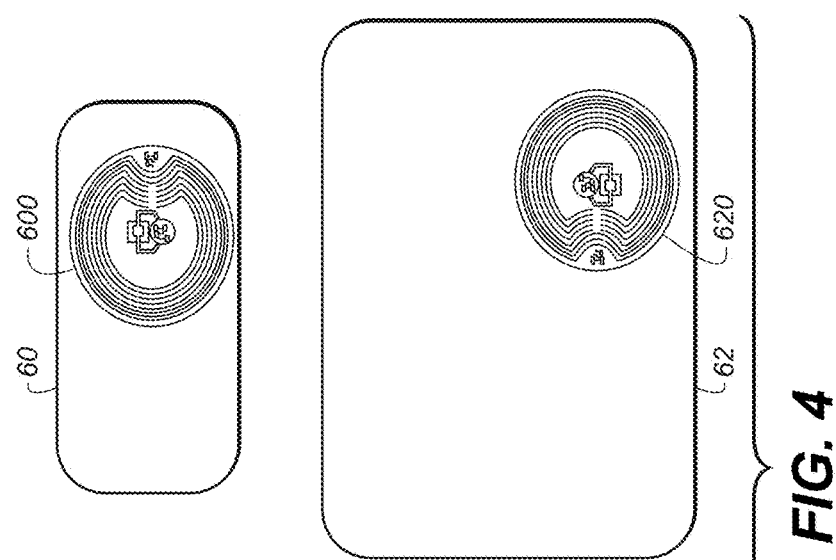
Figure 4:
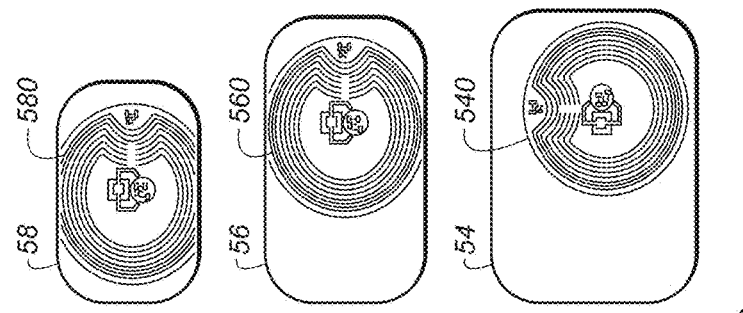

FIGS. 4 and 5 show a few examples of flexible intra-oral dental plates provided with RFID/NFC identification tag in accordance with the present invention. FIG. 4 shows carrier plates 54, 56, 58, 60, 62 of different sizes. The plates are shown without disposable sachets or envelopes in which carrier plates are normally enclosed when the practitioner places them in the patient's mouth for exposure to X-rays.

Each plate bears a respective integrated circuit 540, 560, 580, 600, 620 constituting an RFID/NFC tag. The RFID/NFC tag is disposed immediately on the plate's surface and can be secured thereon by adhesive, for example. In FIG. 4, the tags are secured immediately on a rear side of the plates. The tags can be affixed to different locations of the plates depending on the plate's size. In FIG. 5, a plate 64 has an RFID/NFC tag 640 affixed immediately to a frontal side of the plate such that information about manufacturer and plate's sue is also visible. FIG. 5 shows an embodiment with an RFID/NFC tag affixed to a frontal side of a plate of smaller size. It can be appreciated that, in accordance with embodiments of the present invention, the RFID/NFC tag could be affixed immediately to the rear side of a plate.

A suitable RFID/NFC tag can include a type of commercially available RFID transponder, e.g., HF 15.times.15 mm Dry Inlay, sales code 3001059, manufactured by UPM Raflatec, Finland. Other commercially available transponders can be used as well. A suitable interrogator can similarly be a commercially available product, e.g. HNI002 HF, manufactured by ClarlDy Solutions, Inc., Taiwan.

Figure 6:
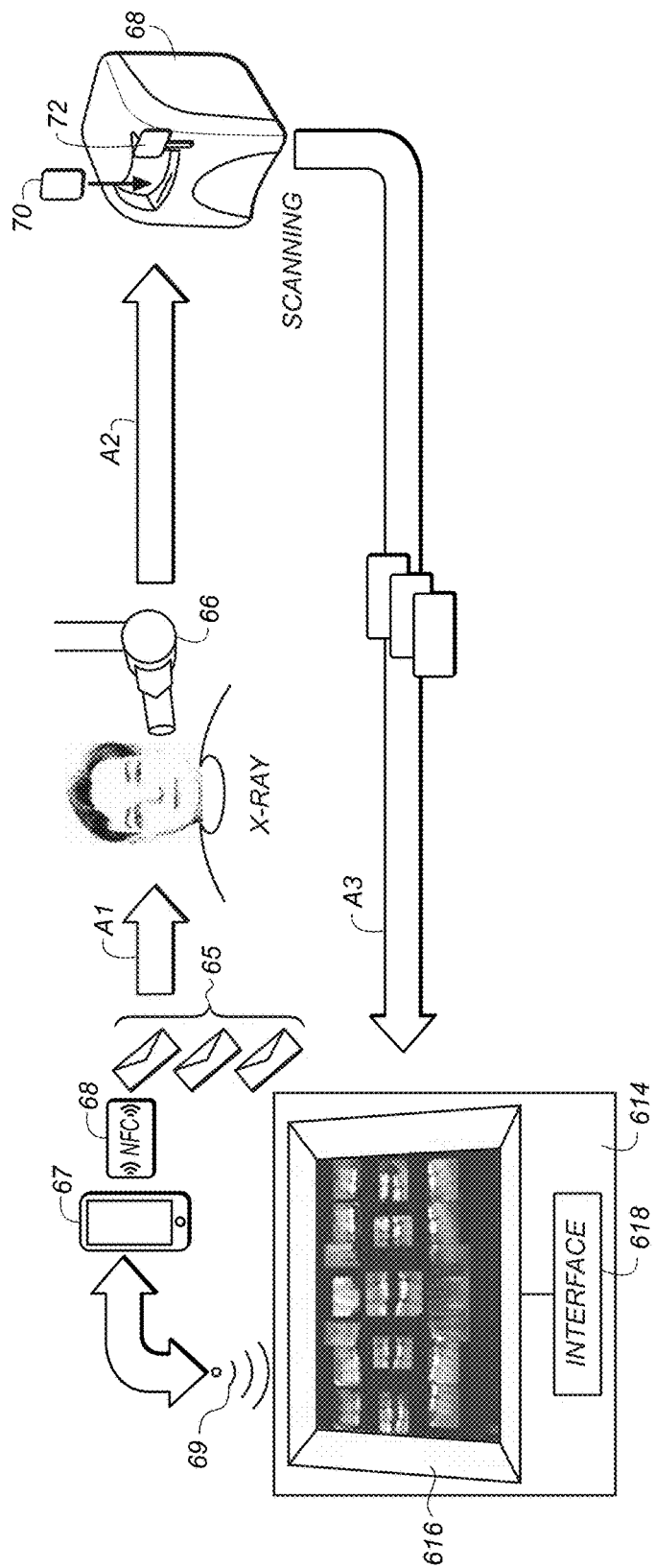
FIGS. 6 and 7 show a working cycle in which tagging of carrier plates as well as display of scanned X-ray images is carried out by a mobile communication device.

In FIG. 6 is depicted a working cycle suitable for processing information carrier plates by using mobile communication device for tagging of RFID/NFC tags affixed to the carrier plates in accordance with an embodiment of the present invention.

A processing and acquisition station (PAS) 614 has an interface 618 coupled with a monitor 616 on which are displayed images acquired during previous scanning. It is seen also that a plurality of intra-oral information carrier plates 65, enclosed in disposable envelopes, proceed as shown by arrow A1, front the processing and acquisition station to X-ray generator 66. The physical location of the processing and acquisition station can be distant from the location of the carrier plates.

The plates intended for exposure are not yet imaged, i.e. they do not carry images, because any previously obtained image were erased from their surface after scanning. Each plate is provided with an RFID/NFC tag that has its memory loaded with permanent information referring to manufacturing data and plate size. The memory is also loaded with temporary information that can be updated by the tagging device in the course of the working cycle.

In accordance with the system as a suitable tagging device here is employed mobile communication device, e.g. smartphone 67, which communicates via a wireless NFC channel 68 with memory of the RFID/NFC tag. The mobile tagging device is also in wireless communication for example via a Wi-Fi channel 69 with the processing and acquisition station 614. This mobile tagging device, which is intended for tagging the carrier plates before their exposure to X-rays will be referred-to further as a primary tagging device.

Among temporary information writable in the memory of the affixed RFID/NFC tag by the primary tagging device is data such as first scan date, scan count and scan status. Scan status can include information such as Scanned and Erased or Tagged and Ready for Exposure, for example.

The physical location of the carrier plates and the tagging device can be distant from the processing and acquisition station and it is preferable that the mobile communication device is located in proximity to an X-ray generator 66, such that the plates can be tagged and the tagging information can be delivered to the processing and acquisition station immediately before exposure to X-rays.

The plates are put in the mouth of a patient nearby the teeth to be examined. Upon completing X-ray exposure, the plates pass, as shown by an arrow A2, to the scanning station for scanning in a scanner 68. Before scanning the envelopes are removed from the plates. One such plate which is ready for insertion into entry slot of the scanner is designated by numeral 70; the plate itself may also include other useful information, such as a size or number indicative of size, for example. The plate is shown being ready for insertion into the entry slot of the scanner. A secondary tagging device designated by numeral 72 is deployed at the scanner, preferably housed within the scanner, and it is in communication with the primary tagging device and/or computer and/or processing and acquisition station. The secondary tagging device 72 not necessarily should be a NFC device, so far as it enables wireless communication with the memory of the RFID/NFC tags affixed to the carrier plates as well as it is able to communicate wire or wireless with the primary tagging device and/computer and/or host workstation that is associated with the treatment room.

The secondary tagging device has an antenna communicating with the respective antenna of the RFID/NFC tag affixed to the plate, so that information stored in the tag's memory is readable and can be available to the practitioner on the monitor of the working station or, if the scanner has a dedicated display, at the scanner itself, or on the display of the primary tagging device itself. When the plate passes scanning the first time, the secondary tagging device writes the first scan date in the memory of the RFID/NFC tag. Upon each subsequent scanning operation, the secondary tagging device sends a signal that is received by the antenna of the RFID/NFC tag and by virtue of this provision incrementing of the scan count stored in the tag's memory takes place. This signal also updates the scan status of the plate, i.e. whether the plate has already been scanned or not. One should appreciate that this feature makes it possible to more easily monitor the service life of the plate and its scan status.

For example, the scan count can be compared against a threshold count value and the result reported when a plate exceeds the threshold. Optionally, the tagging device can be set up to disable use of a plate having a scan count above a threshold value.

When scanning is completed, the scan count is updated in the tag's memory and the obtained image is sent by the secondary tagging device to the processing and acquisition station (PAS) and to the primary tagging device. This is indicated by an arrow A3. As said before, if the scanner is provided with a display, the image can be viewed on its display as well. Then, the plate is erased and proceeds back to the processing and acquisition station. At the working station, the erased plates are put into disposable envelopes and are ready for the next working cycle.

Figure 7:
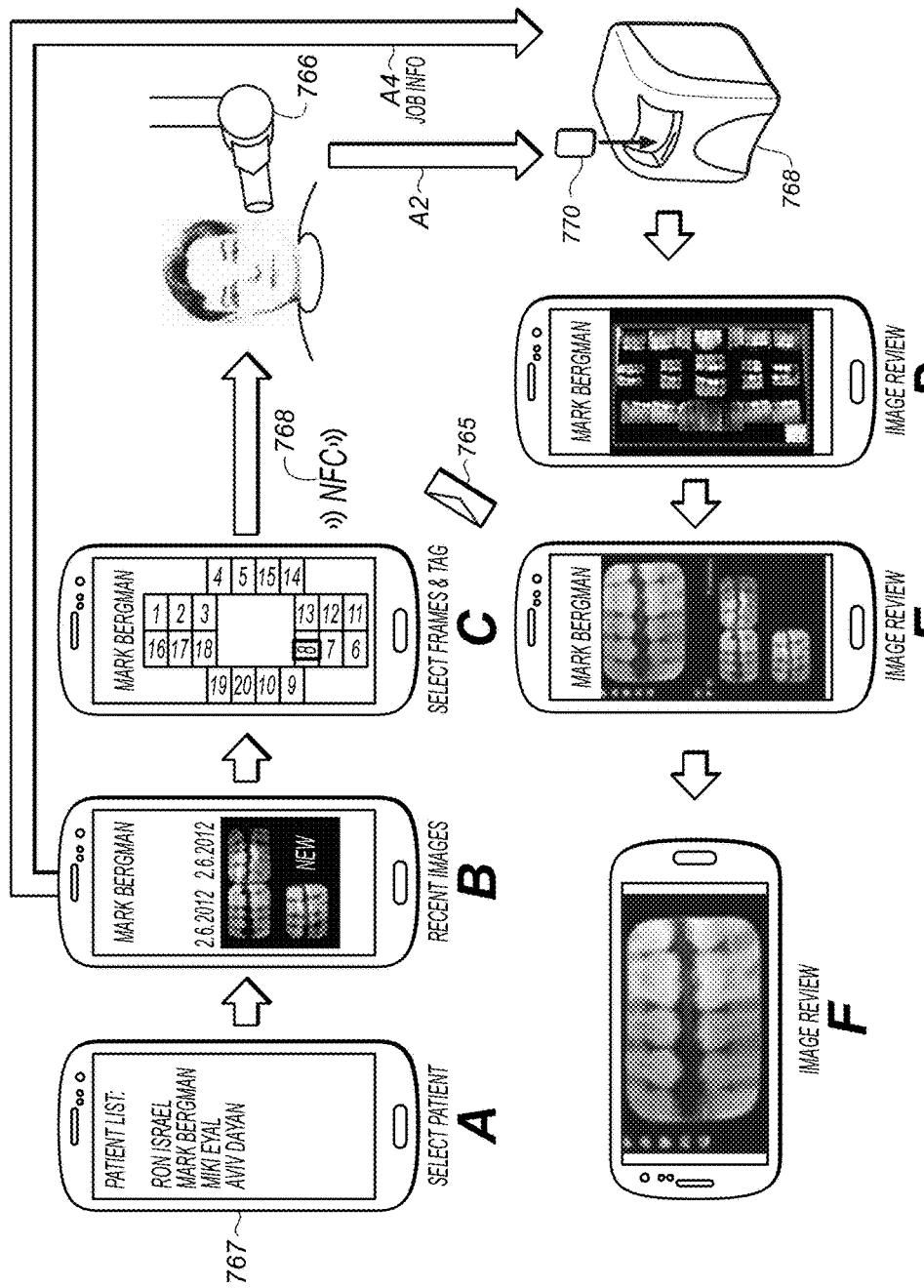

In FIG. 7 there is shown the tagging procedure carried out with the aim of mobile communication device 767 functioning as a primary tagging device. In particular, a series of suitable GUI templates is seen that can be associated with a study folder.

The sequence of the GUI templates is displayed in accordance with a suitable data management software (SW) application, loaded in the mobile communication device before its use.

So, for example in FIG. 7, at Step A is seen an initial GUI template intended for presenting list of patients (Patient List:) which were treated before by a practitioner. Once the required name has been selected and tapped (e.g. Mark Bergman) the next GUI template appears on the screen of the mobile communication device. The new GUI template is seen in FIG. 7, at Step B. It is seen in particular, that on top of the new GUI template appears name of the selected patient (Mark Bergman). This GUI template also displays three images of teeth of this particular patient as well as the date (Feb. 6, 2012) when these images have been acquired during previous treatments. It is also seen that an empty window designated as NEW is provided. This window is assigned and reserved for the image, which will be obtained during the current treatment.

Simultaneously with assigning the NEW window a signal with a Job information (e.g. Job number) is generated and this signal is sent by the first tagging device via a wireless communication channel to a scanner 768 as designated by an arrow A4.

By tapping on the NEW window the next GUI template is called. This GUI template is seen in FIG. 7, at Step C. The new template consists of empty windows arranged in a pattern compatible with the normal arrangement of human teeth. When this template opens, it also can display patient identification details (Mark Bergman, see on top) as well as date of treatment and the like. During the input step, the practitioner can select those windows on the template that refer to teeth to be treated, and then he taps and highlights the selected windows. In the electronic template shown in FIG. 7, at Step C, a window for teeth number 8 has been selected and highlighted.

Once the sequence of GUI electronic templates is completed the tagging device is brought in close proximity to the information carrier plate assigned for selected patient and the inputted information is automatically sent by a wireless NFC channel 768 to a particular information carrier plate 765, such that this plate becomes unequivocally assigned to a particular tooth of a particular patient.

At the next step the assigned carrier plate is exposed to X-rays generated by an X-rays generator 766 and then the exposed carrier plate 770 proceeds to a scanner 768 as designated by an arrow A2.

As soon as the scanning is completed the electronic image along with details of the patient is transmitted to the mobile electronic device and is displayed on its display a shown in FIG. 7, at Steps D, E and F.

During the tagging step, which may take place at any suitable location, where flexible carrier plates are available, the primary tagging device writes temporary information into the memory of the RFID/NFC tag. The temporary information comprises inter alia, job number or other type of job identifier that relates to a particular imaging session or "job", resolution, destination address. Furthermore the temporary information comprises patient identification data that is up-loaded from the database system, to which the tagging device has access. The patient identification data is also accessible in the data base at the processing and acquisition station. This data refers to job number or other type of job identifier, which is in fact a random number written in the memory of the RFID/NFC tag. When scanning is completed and the obtained image is available from the scanner, it is displayed on monitor 16 of the working station, as well as on the display of the mobile communication device.

Now with reference to FIG. 8 an embodiment of a system for intra-oral computed radiography in accordance with the present invention will be explained.

In this embodiment the system comprises the following basic elements;

a) a plurality of working stations 75, 76, 78 each of which being equipped with a treatment chair and X-ray generator and each having a respective processing and acquisition station 80, 82, 84 having access to appropriate application data management software;

b) a plurality of scanning devices 86, 88, 90 provided with respective secondary tagging devices 860, 880, 900;

c) a plurality of flexible information carrier plates 92 having respective RFID/NFC tags affixed immediate to one of their sides;

d) a plurality of primary tagging devices 800, 820, 840 associated with and being in NFC communication with respective working stations PAS 80, 82, 84, operable for tagging information carrier plates before the plates are exposed to X-rays; and e) a server 94 providing access to a database 940 and appropriate data management system.

Figure 8:
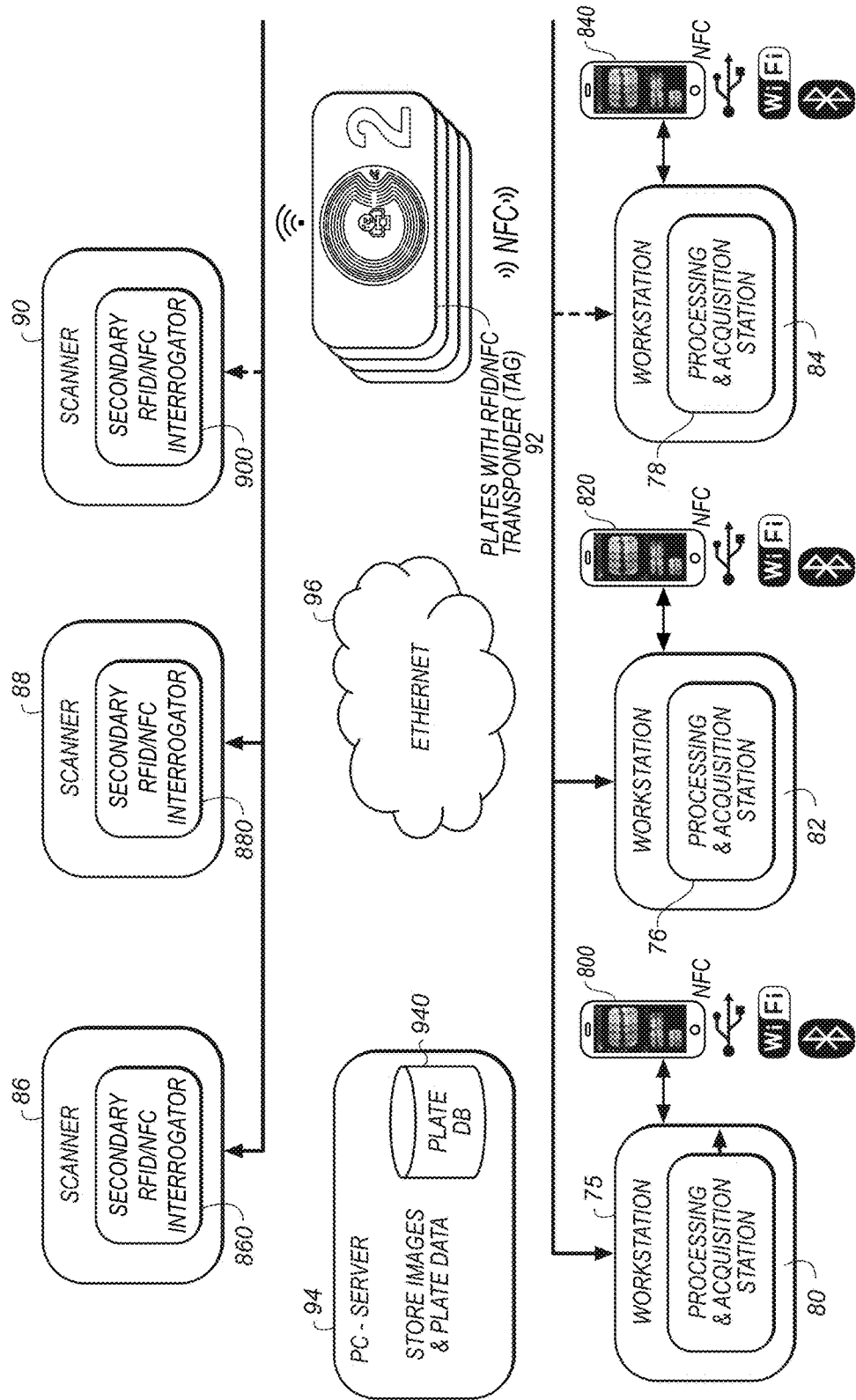
FIG. 8 depicts schematically a system for intra-oral computed radiography employing mobile communication device in accordance with the present invention.

As is shown in FIG. 8, working stations, scanners, and server can communicate between each other via connection over an appropriate network, e.g., Ethernet network 96. With network connection, messages can readily be sent by the secondary tagging devices employed in the scanners to the processing and acquisition stations, as well to the primary tagging devices and vice versa. Besides of this, files with scanned images can be sent for archiving and storing in the database.

In the system of FIG. 8, primary tagging devices 800, 820, 840 can communicate with respective processing and acquisition stations 80, 82, 84, as well as with the secondary tagging devices 860, 880, 900. In one embodiment, this communication uses a USB connection. Wireless communication is available in an alternate embodiment, through Wi-Fi (Institute of Electrical and Electronics Engineers (IEEE) 802.11 standard, generally termed Wi-Fi) or through Bluetooth connection. One should appreciate that these devices can communicate as well through any other suitable wire or wireless connection that enables communication and exchange of data.

It is noted that the system of the present invention may have more or fewer than three working stations and three scanners as depicted in FIG. 8. For example, one can contemplate a system comprising a single working station and one scanner, or one working station and several scanners, or several working stations and one scanner. The number of working stations need not be equal to the number of scanners and vice versa. It is appreciated that using of mobile communication device as a tagging device readily available at any location outside of the working station saves practitioner time required for tagging.

It is noted that both primary and secondary tagging devices are operable to both read and write or amend information stored in the memory of RFID/NFC tags in order to update it as part of the tagging operation.

Figure 9:
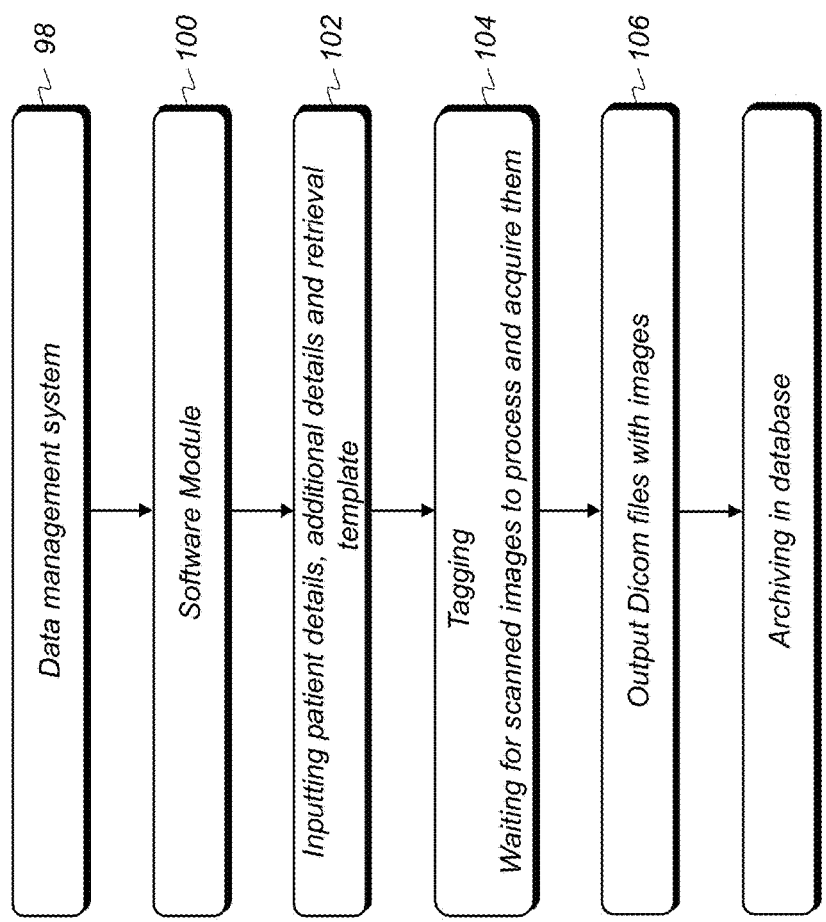
FIG. 9 is a block diagram of the input, acquisition, and output of data circulating in the system shown in FIG. 8.

FIG. 9 shows a block diagram of the data flow taking place in the system of the present invention. The flow of data comprises input, processing and acquisition, and output of data. This flow is enabled and controlled by data management system software 98, e.g. a department patient management system. This software should be loadable, e.g. as an Android application, to the mobile communication device.

The management system is provided with a database for archiving data and with appropriate software module 100 for acquisition of images and data. One example of suitable software is KDIS (Kodak Dental Imaging Software).

The Input step carried out with the aim of tagging device is designated by reference numeral 102. The data inputted by the software module is downloaded from the database. This data comprises patient details, previous treatment detail, and previously stored images. The input step 102 also comprises retrieval of appropriate templates that should be completed prior to treatment.

The processing and acquisition of data is designated by reference numeral 104. This step is associated with the tagging and with the scanning and with the sending of scanned image from scanner to working station and to mobile communication device. Furthermore, this step comprises also reporting of events, like for example the necessity of assigning new job number or other type of job identifier, which should refer to the data downloaded from the database. The job number is an assigned number, such as a random number that can be generated by the data managing system itself or can be taken from the stock of previously generated and stored random numbers.

The output of data is designated by reference numeral 106. This step takes place upon completing the scanning and comprises acquisition of the image and sending it to the primary tagging device and to database for archiving. The acquired image is archived preferably as DICOM file (Digital imaging and Communications in Medicine Format Bitmap file).

Figure 10:
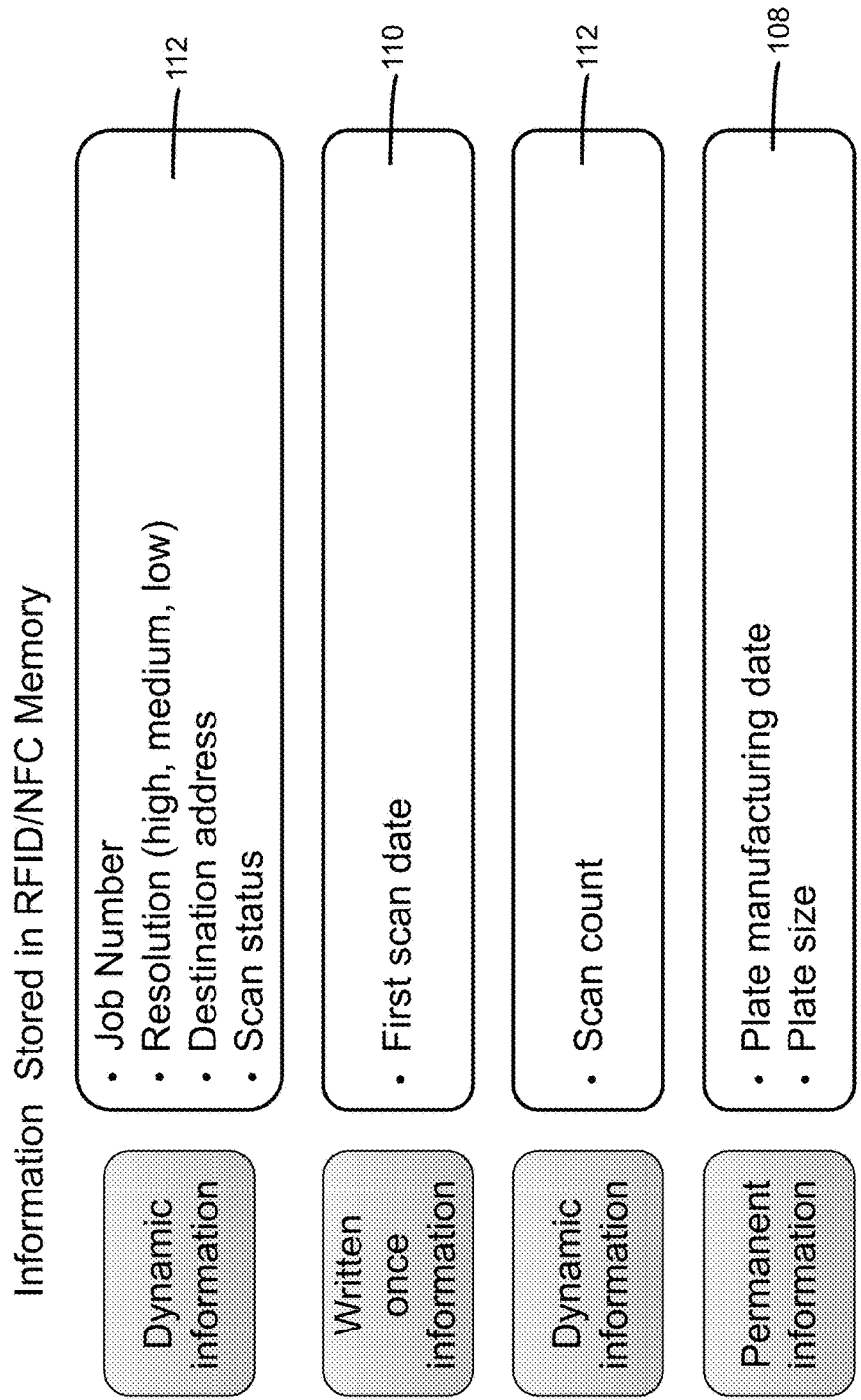
FIG. 10 depicts schematically the structure of information stored in the memory of an RFID/NFC tag attached to flexible carrier plates shown in FIGS. 4 and 5.

In FIG. 10, there is shown the structure of information that is stored in the memory of the RFID/NFC tag according to one embodiment. As previously stated, this information consists of permanent data, which is written once and is not amended during the working cycle, and of temporary data, which can be amended during the working cycle by tagging. This data will be referred to further as dynamic data.

The permanent data comprises data written by manufacturer of the plate and data written by the tagging device. The dynamic data is always written by the tagging device.

So, for example, the permanent data written by the manufacturer comprises data 108 referring to manufacturing date, plate size and type. The memory allocated to data 108 comprises two blocks of 32 bits each in one embodiment.

Permanent data which is written once by the secondary tagging device at the scanning station comprises data 110, which stores the activation date (first scan date). Size and other characteristics of the plate can also be stored in the permanent data. The memory allocated for this comprises one block of 32 bits in one embodiment.

Dynamic data is designated by reference numeral 112 and may comprise, for example, the following types of data: job number or other type of job identifier, required resolution of scanning (high, medium, low), destination address (to which working station the scanned image should be sent for acquisition), scan status (whether or not the plate has already been scanned) and scan count (number of scans the plate has undergone). The memory allocated for dynamic data comprises five blocks of 32 bits each in one embodiment.

Depending on type, the dynamic data can be amended either by the primary tagging device, or by a secondary tagging device. So, for example, scan count and scan status is amendable by the secondary tagging device at the scanner, while job number or identifier, resolution and destination address are amendable by the primary tagging device.

The dynamic data is recognizable by the software application available at the processing and acquisition station, such that patient identification data extracted from the database during the tagging step is always linked with the job number or other type of job identifier that is written in the memory of the RFID/NFC tag.

During the tagging process, a job number or other type of job identifier is also generated. The job number is written in the memory of the RFID/NFC tag by the primary tagging device and is stored by the software application in association with the extracted patient identification data. Thus, a particular job number or other identifier constitutes a link between a certain plate and between details of treatment of a particular tooth of a particular patient. With this arrangement, it would be possible to positively identify the plate and attribute it to a particular patient and to a particular treatment. Eventually, all required windows in the electronic template GUI of FIG. 7 are highlighted by the practitioner in accordance with the treatment plan and linked by the job number with respective carrier plates.

For certain treatment plans, e.g., whole mouth shot, selection of windows during the tagging process might take place automatically such that identification data extracted from the database during the input step is always linked with the job number or other type of job identifier that is written in the memory of the RFID/NFC tag.

Figure 11:
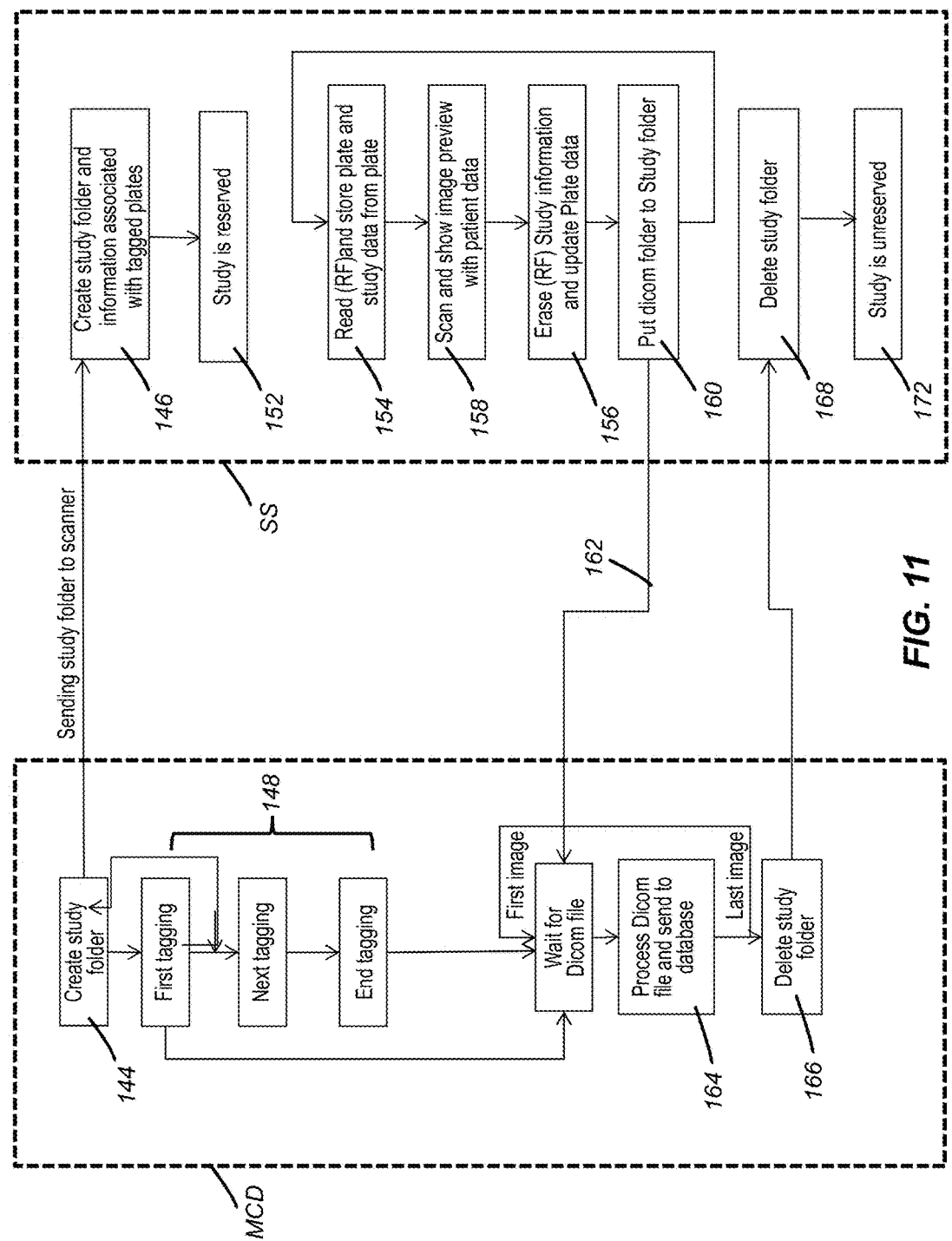
FIGS. 11-13 show block diagrams of working cycles of the system in accordance with alternative embodiments of the invention.

Referring now to FIG. 11 there is shown a block diagram explaining interaction between mobile communication device and scanning station. This interaction takes place during computed intra-oral radiography in accordance with an embodiment of the present invention. In this embodiment the mobile communication device functions both as tagging device and as a suitable medium for storing information being entered by a practitioner during the tagging step and for storing images produced during the scanning. In other words in this embodiment the mobile communication device is autonomous, since it by itself functions both as tagging device and as a processing and acquisition station.

In practice this option may be suitable for a small, autonomous clinic, which is not equipped with or otherwise not connected to a server.

In FIG. 11 those steps which refer to functioning of mobile communication device are shown within a rectangle designated by an abbreviation MCD and those step which refer to functioning of the scanning station are shown within a rectangle designated by an abbreviation SS.

In this embodiment, information carrier plates have RFID/NFC tags with memory that stores written permanent information 108 (manufacturing date and plate size), written-once information 110 (first scan date) and various types of dynamic information 112 (scan count and scan status, job number, resolution, destination address).

In the beginning of working cycle, the processing and acquisition application software downloaded in the mobile communication device prepares the working cycle. In a step 144, a study folder is formed with patient identification information (patient data) and other previous treatment study data (if they were previously stored in the mobile device). The folder also indicates details of the current treatment, like tooth number, scan resolution, shot type (full mouth shot or single shot) and the like. Simultaneously with creation of the study folder, the software application issues a unique reference associated with this folder and with the required treatment. This reference or job number can be an assigned or a random number generated by the software itself or taken from the stored stock of random numbers. The study folder, along with the treatment details (job details), e.g. tooth number, scan resolution and the like is sent to the scanner which receives it and temporarily stores it as designated by a step 146. All this data is sent via Wi-Fi channel. One should appreciate that this data could be sent also via Bluetooth channel, or via a local net or wire or via a cable channel.

Then, in a step 148, tagging is initiated and the plates, enclosed in disposable envelopes, are sequentially tagged by the primary tagging device. During tagging, the above mentioned dynamic information is written in the memory of the RFID/NFC tag. After the all plates have been tagged, they proceed to exposure to X-rays as explained in connection with the previous embodiment.

The exposed plates are extracted from the patient's mouth, their envelopes are torn open, and the plates proceed to a scanner in which the study folder, job details, and job number have been already stored. The software at the mobile device functioning as primary tagging device issues the instruction "reserve scanner". After the scanner is reserved, the first plate with RFID/NFC tag is inserted into the scanner. The secondary tagging device at the scanning station reads dynamic information written in the memory of the RFID/NFC tag and increments the scan count, thus increasing the instant scan count. Furthermore, the plate is scanned at the resolution indicated in the dynamic information and the secondary tagging device deletes the present job number. Furthermore, the secondary tagging device updates the status of the plate to "scanned".

The obtained image is displayed on the scanner's LCD monitor and on the screen of the first tagging device along with patient identification data. The obtained image is stored in the study folder as a DICOM file with a header containing patient identification information, job details and job number. The sequence of processes for scanning, processing, and storing the obtained image is shown in steps 152, 154, 156, 158, and 160 of FIG. 11.

The primary tagging device waits until it receives the saved DICOM file for processing and display in an appropriate window on the template. Upon completing the acquisition, the DICOM file proceeds to the memory of the mobile communication device for archiving in a database. This sequence of events is designated by steps 162,164 and it repeats with all plates that were tagged and scanned as part of the same treatment session.

When the plate is scanned, it can be erased so that it is ready to proceed either to the working station or to the treatment room, where X-ray generator is available. Here, it is enclosed into a disposable envelope to be available for the new working cycle.

When the last DICOM file associated with the treatment session is archived, the software application deletes the created study folder from the processing and acquisition station, from the memory of the primary tagging device and from the scanner memory. The acquisition step comes to its end and the scanner receives status "unreserved". This sequence is shown in steps 166, 168, and 172.

Sending information to mobile communication device from scanner is effected via Wi-Fi channel. It could be sent also via Bluetooth channel, or via a local net or wire or via a cable channel.

With this arrangement, wherein each carrier plate has an RFID/NFC tag immediately affixed to one side, it is always possible to identify, monitor, and track the plates during the entire working cycle, whether or not they are enclosed within the envelopes irrespective whether the plates are physically available. Having the RFID/NFC tag applied to the plate can also help to assist in plate orientation, so that the exposure source is on the side of the phosphor coating, rather than on the opposite side that has the RFID/NFC tag. Because the RFID/NFC tag stores both permanent and temporary information, it is possible to unequivocally identify the plates during each part of the working cycle, whether or not the plates are scanned. This is possible because the RFID/NFC tag has a unique job number associated with the patient identification information and with job details.

Figure 12:
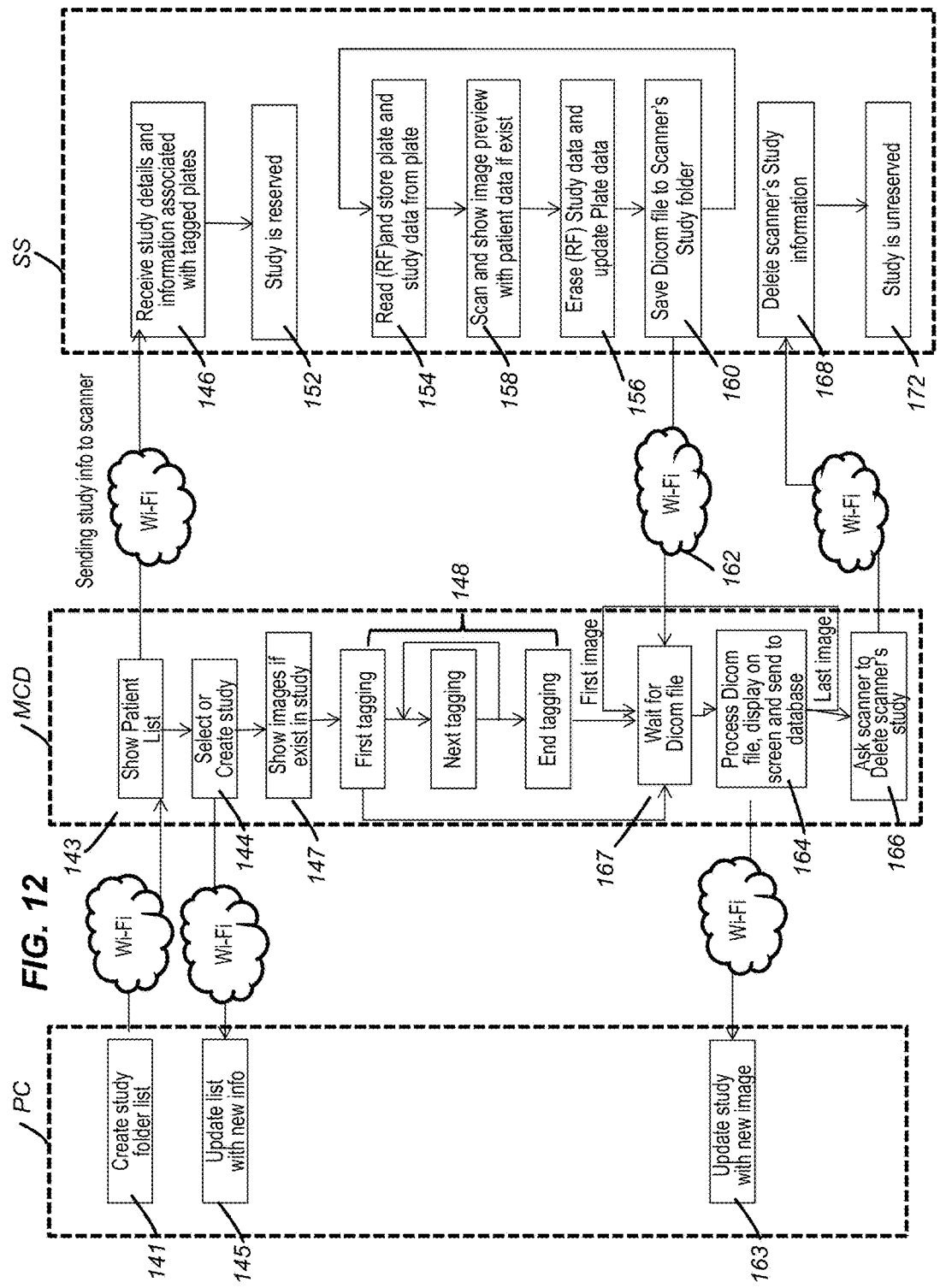

In a still further embodiment, which is presented in FIG. 12, the mobile communication device is connected to a processing and acquisition station equipped with a dedicated PC, which might be connected to a server and a database (not shown).

In FIG. 12 the processing and acquisition station is schematically shown by a rectangle delimited by dotted line and it is designated by an abbreviation PC.

In principle the interaction between mobile communication device and the scanning station in accordance with this embodiment is similar to the interaction described above with reference to FIG. 11 and therefore for the sake of brevity the same numerals are used here to designate the same steps.

However in this embodiment before executing step 144 the mobile communication device receives patient list from the PC, in which has been already created study folder list. Creation of a study folder and transmitting list of patients via Wi-Fi channel from the PC to mobile communication device is schematically designated by numerals 141 and 143 respectively.

It is shown also in FIG. 12 that as soon as a certain study has been selected or created by a practitioner, the mobile communication device sends via Wi-Fi channel an updated list of patients to the PC. This step is designated by numeral 145.

An option of displaying images, which have been stored in the PC in connection with a certain study, is foreseen in the mobile communication device. This option is designated by numeral 147 and it can be executed before tagging.

In the end of the working cycle after the DICOM file with new images has been created and displayed on the mobile communication device this file is transmitted by the mobile communication device via Wi-Fi channel to the PC, where the relevant case study is updated and stored. This step is designated by numeral 163.

Figure 13:
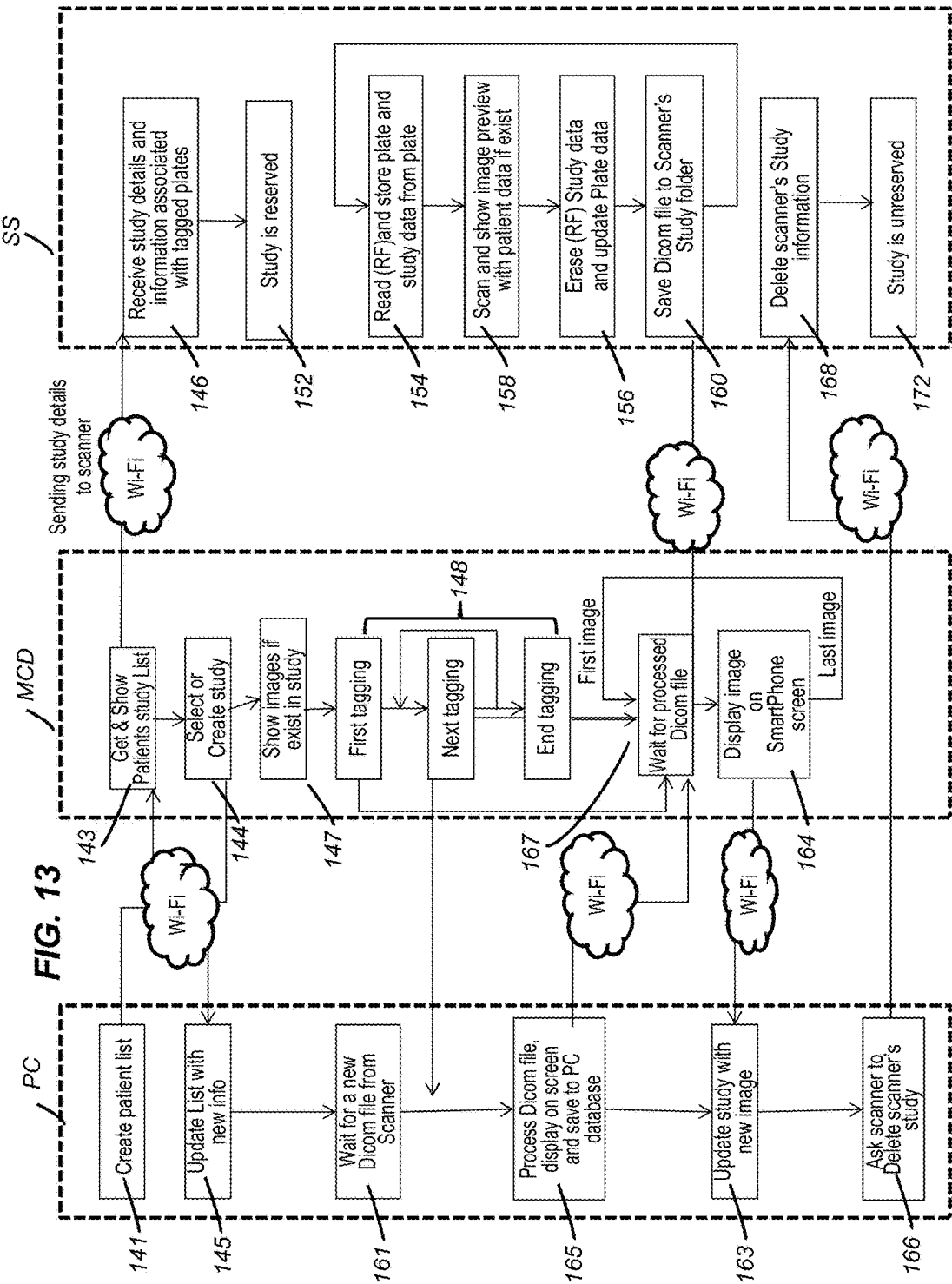

In a further embodiment of the invention as shown in FIG. 13 the interaction between mobile communication device, PC and scanning station comprises an option of processing the relatively crude images produced at the scanning station.

This processing comprises inter alia filtering of undesired artifacts and/or improving of contrast and this can be implemented by using a dedicated processing module within the PC software. Processing the images allows to practitioner more objective diagnostics and selection of suitable course of treatment. An example of suitable image processing software is Eclipse IP.

One should appreciate that the rest of interaction between mobile communication device and the scanning station in accordance with this embodiment is similar to the interaction described above with reference to FIG. 11 and therefore for the sake of brevity here the same numerals are also used to designate the same steps.

As shown in FIG. 13 upon saving a DICOM file with scanned images at step 160 this file is transmitted via Wi-Fi channel to the PC, which waits for the file as designated by a step 161. Then the transmitted file is image processed at a step 165 and is saved to a PC database. Then at a step 163 the processed images are sent to the relevant case study folder which is updated.

The processed images are also sent via Wi-Fi channel to the mobile communication device, which waits them at a step 167 before they are displayed at the mobile communication device at step 164.

Upon updating the relevant study folder in the PC database a command to delete this study folder is issued and transmitted by PC via Wi-Fi channel to the scanning station.

This step is designated by the reference numeral 166.

Other benefits of the present invention that result from using the NFC mobile communication device as tagging device as well as RFID/NFC tag with both permanent and temporary information include the capability for example to monitor plate service life by establishing manufacturing date, first activation date, and number of scanning cycles passed. Storing this data can help the practitioner to monitor overall usage and manage plate allocation and replacement. In one embodiment, the scan count is checked at the beginning of each working cycle and, if appropriate, the Scan status field in memory is flagged as Past Useful Life or identified as Unusable.

The invention has been described in detail with particular reference to certain preferred embodiments thereof, but it will be understood that variations and modifications can be effected within the scope of the invention. For example, various types of data can be stored in the RFID/NFC tag or in the memory circuitry that is used by the interrogator.

Furthermore, instead of smartphone one could use as suitable tagging device tablet or any other available NFC technology based mobile communication device.

Thus, there is provided a system and method for identification, monitoring, and tracking of flexible information carrier plates used in intra-oral dental computed radiography.

The mobile communication devices become more and more popular and all known benefits associated with their use could be achieved in addition to their functioning as mini PC computers having RFID capabilities.

By virtue of the present invention it is possible to treat patients faster, more efficiently, more conveniently and more secure while the amount of patients treated in the same treatment room could be increased.

Furthermore, the treatment becomes easier since there is no need in using mouse.

Still further benefits of the present invention are associated with improved security of treatment and improved quality control. For example, benefits are achieved by: a) Tracking the number of cycles associated with the being used plate and its timely replacement by a fresh one; b) Tracking number of working cycles associated with the being used plate and its disinfection before running the next cycle; c) Plates size detection; d) Tracking manufacturing date; e) Elimination of possibility for scanning the exposed plate in a wrong scanner; f) Warning if period of time between exposure and scanning of the same plate exceeds certain preselected threshold; and g) Warning if time elapsed from the last scan exceeds certain preselected threshold and therefore the plate should be erased.

The invention claimed is:

1. A system for obtaining an intra-oral X-ray image of a patient, comprising:
    one or more information carrier plates, each information carrier plate having a NFC/RFID tag affixed to the information carrier plate, the NFC/RFID tag having a memory;
    at least one primary tagging device operable to read and write temporary information into the memory of the NFC/RFID tag over a first communication channel; and
    at least one scanner in communication with a secondary tagging device that is operable to read and write temporary information saved in the memory of the NFC/RFID tag over a second communication channel, wherein the at least one primary tagging device is a mobile communication device.

2. The system of claim 1, in which the second tagging device is located within the scanner.

3. The system of claim 1, in which the primary tagging device is in communication with a computer.

4. The system of claim 1, in which at least the first communication channel is wireless channel.

5. The system of claim 1, in which the mobile communication device is selected from the group consisting of a smartphone and a tablet.

* * * * *